(12) United States Patent
Shimel et al.

(10) Patent No.: US 10,864,333 B2
(45) Date of Patent: Dec. 15, 2020

(54) MEDICAL LIQUID WARMER WITH AUXILIARY TEMPERATURE SENSOR

(71) Applicant: ENTHERMICS MEDICAL SYSTEMS, Menomonee Falls, WI (US)

(72) Inventors: Kyle Shimel, Waukesha, WI (US); William J. Hansen, Pewaukee, WI (US); John Matthew Rotterman, Waynesville, OH (US)

(73) Assignee: Enthermics Medical Systems, Menomonee Falls, WI (US)

( * ) Notice: Subject to any disclaimer, the term of this patent is extended or adjusted under 35 U.S.C. 154(b) by 329 days.

(21) Appl. No.: 15/475,708

(22) Filed: Mar. 31, 2017

(65) Prior Publication Data

US 2017/0281879 A1    Oct. 5, 2017

Related U.S. Application Data

(60) Provisional application No. 62/316,972, filed on Apr. 1, 2016.

(51) Int. Cl.
| | |
|---|---|
| *A61M 5/44* | (2006.01) |
| *A61J 1/10* | (2006.01) |
| *G01K 15/00* | (2006.01) |
| *G05D 23/19* | (2006.01) |

(52) U.S. Cl.
CPC ............. *A61M 5/445* (2013.01); *A61J 1/10* (2013.01); *G05D 23/1931* (2013.01); *A61M 2205/3368* (2013.01); *A61M 2205/502* (2013.01); *A61M 2205/52* (2013.01); *A61M 2209/084* (2013.01)

(58) Field of Classification Search
CPC ............ A61M 5/445; A61M 2209/084; A61M 2205/52; A61M 2205/3368; G05D 23/1931; A61J 1/10
See application file for complete search history.

(56) References Cited

U.S. PATENT DOCUMENTS

| | | | |
|---|---|---|---|
| 4,923,681 A | 5/1990 | Cox et al. | |
| 6,384,380 B1 * | 5/2002 | Faries, Jr. ............ | A61G 12/001 219/385 |
| 6,536,943 B1 * | 3/2003 | Feske ..................... | C09K 21/00 252/607 |
| 2001/0042743 A1 * | 11/2001 | Faries, Jr. ............. | A61F 7/0241 219/400 |
| 2003/0082069 A1 | 5/2003 | Kuzyk | |
| 2003/0114795 A1 * | 6/2003 | Faries, Jr. ............... | A61M 5/44 604/113 |
| 2013/0197437 A1 * | 8/2013 | Faries ..................... | A61M 5/44 604/113 |

* cited by examiner

*Primary Examiner* — Regis J Betsch
*Assistant Examiner* — Jeremy A Delozier
(74) *Attorney, Agent, or Firm* — Boyle Fredrickson S.C.

(57) ABSTRACT

An auxiliary sensor can be used to measure the temperature of individual products in a heating cabinet. By arranging the temperature sensor with respect to the low mass thermal conductors and insulators, the sensor can be focused on the product to obtain the proper temperature irrespective of the immediate environment whether it is at room temperature or even within the heating cabinet.

20 Claims, 4 Drawing Sheets

MEDICAL LIQUID WARMER WITH AUXILIARY TEMPERATURE SENSOR

CROSS REFERENCE TO RELATED APPLICATION

This application claims priority to U.S. provisional application No. 62/316,972 filed Apr. 1, 2016 and hereby incorporated by reference.

BACKGROUND OF THE INVENTION

The present invention relates to warming systems for medical fluids, and in particular, to a warming cabinet with an auxiliary temperature sensor separate from the temperature sensor of the warming cabinet.

Warming cabinets for use in the medical industry are frequently used to maintain intravenous fluids at or near body temperature in order to maintain patient normothermia from admission to discharge. Maintaining the temperature and quality of intravenous fluids improves patient recovery, decreases blood loss, reduces surgical site infections, and reduces the length of hospital stays.

While warming cabinets typically ensure that product in the cabinets is quickly brought up to the proper body temperature, product recently introduced into the cabinets may not have achieved the proper temperature, allowing undesirably cool product to be introduced into the patient. In addition, if product is returned to the cabinet, how long it needs to remain in the cabinet may be unclear. This is particularly a problem because recently introduced product may be toward the front of the cabinet.

SUMMARY OF THE INVENTION

The present invention provides an auxiliary sensor that can be used to, measure the temperature of individual products in a heating cabinet. By arranging the temperature sensor with respect to the low mass thermal conductors and insulators, the sensor can be focused on the product to obtain the proper temperature irrespective of the immediate environment whether it is at room temperature or even within the oven.

In one embodiment, the present invention may be an auxiliary temperature monitoring system for measuring the temperature of an IV bag held within a warming cabinet, the system comprising a housing having an internal cavity; a heater adapted to heat the internal cavity; a sensor detecting a temperature of the internal cavity; and an auxiliary temperature device comprising an auxiliary housing, a heat collection plate supported by the housing and having an upwardly exposed upper surface configured to support the IV bag therein, and an auxiliary sensor configured to approximate a temperature of the heat collection plate.

It is thus a feature of at least one embodiment of the present invention to determine a temperature of an IV bag within a heating cabinet (or an IV bag just taken out of the heating cabinet) that is independent from the temperature reading of the interior cavity.

A feedback control system may receive the temperature of the internal cavity to control activation of the heater.

It is thus a feature of at least one embodiment of the present invention to utilize the heating cabinet heater for heating the IV bag but utilize the auxiliary temperature device for determining a temperature of the IV bag.

The plate may be sized to contact at least 30 percent of the surface of an IV bag supported by the auxiliary housing. The heat collection plate may have an exposed area greater than 4 square inches or greater than 6 square inches.

It is thus a feature of at least one embodiment of the present invention to allow the heat collection plate to quickly adjust to and equalize with the IV bag temperature when within the internal cavity.

An entire lower surface of auxiliary housing beneath the heat collection plate may be insulated.

It is thus a feature of at least one embodiment of the present invention to isolate measurement of the heat collection plate to an upper surface contacting the IV bag.

The upper surface of the housing has opposed rails along opposite sides of the housing upper surface configured to retain an IV bag.

It is thus a feature coat least one embodiment of the present invention to support the length and width of the IV bags in a manner which facilitates temperature sensing toward a center of the IV bag.

An interior surface of the internal cavity has a releasable electrical connector adapted to receive a first end of a mating second electrical connector connected to the auxiliary temperature device.

It is thus a feature of at least one embodiment of the present invention to take temperature readings while the IV bag is within the interior cavity to reduce heat loss or disruption within the internal cavity.

The second electrical connector may communicate with the auxiliary temperature device through a flexible conductor.

It is, thus a feature of at least one embodiment of the present invention to be able to take temperature readings from outside of the interior cavity, e.g., when space within the interior cavity is limited.

An exterior surface of the housing may have a third electrical connector adapted to receive the second electrical connector wherein an opposite end is connected to the auxiliary temperature device.

It is thus a feature of at least one embodiment of the present invention to be able to take temperature readings of medical product whether or not they are placed within the warming cabinet.

A processor may operate a program stored in memory and communicate with the auxiliary sensor to determine an average temperature of the heat collection plate.

It is thus a feature of at least one embodiment of the present invention to detect an average temperature about an entire area of the IV bag.

The processor may operate a program stored in memory to communicate with a read out button to display the temperature of the auxiliary sensor on a warming cabinet display screen.

It is thus a feature of at least one embodiment of the present invention to display an auxiliary temperature through the heating cabinet's built in controller and display screen.

The processor may further operate the program stored in memory to communicate with a calibration button to compare the temperature of the warming cabinet sensor with the temperature of the auxiliary sensor and subtract a difference between the temperature of the sensor and the temperature of the auxiliary sensor from the temperature of the auxiliary sensor to calibrate the auxiliary sensor.

It is thus a feature of at least one embodiment of the present invention to calibrate the temperature sensor prior to use to adjust for heat loss or external factors affecting the auxiliary sensor.

The housing may be supported on feet extending downwardly from a bottom of the housing that are spaced apart to engage wire racks of the internal cavity therebetween the feet.

It is thus a feature of at least one embodiment of the present invention to balance the housing on a wire rack without tilting the IV bag.

The auxiliary temperature device may not have a heater.

It is thus a feature of at least one embodiment of the present invention to provide a standalone temperature measurement device.

The housing may be sized to contact less than 75 percent of a lower surface of the IV bag supported by the auxiliary housing.

It is thus a feature of at least one embodiment of the present invention to insulate the heat collection plate from the oven racks while supporting the IV bag.

The sensor may be bonded beneath the heat collection plate.

It is thus a feature of at least one embodiment of the present invention to provide an accurate representation of plate temperature without heat loss therebetween.

The heat collection plate may be a conductive metal. The heat collection plate may have a gauge thickness of less than or equal to 0.01 inches.

It is thus a feature of at least one embodiment of the present invention to provide fast conduction of heat from the plate to the sensor.

In one embodiment, the present invention may provide a method of detecting a temperature of an IV bag placed within a warming cabinet comprising a housing having an internal cavity; a heater adapted to heat the internal cavity; and a sensor detecting a temperature of the internal cavity, wherein the temperature is independent of the temperature of the warming, cabinet, and comprising the steps of: placing an auxiliary temperature device comprising an auxiliary housing, a heat collection plate supported by the housing and having an upwardly exposed upper surface configured to support an IV bag therein, and an auxiliary sensor configured to approximate a temperature of the heat collection plate within the warming cabinet; connecting the auxiliary temperature device to the warming cabinet; placing the IV bag on the heat collection plate; pressing the temperature read out button; and displaying the temperature of the heat collection plate on a display.

These particular objects and advantages may apply to only some embodiments falling within the claims and thus do not define the scope of the invention.

DETAILED DESCRIPTION OF THE PREFERRED EMBODIMENT

Figure 1:
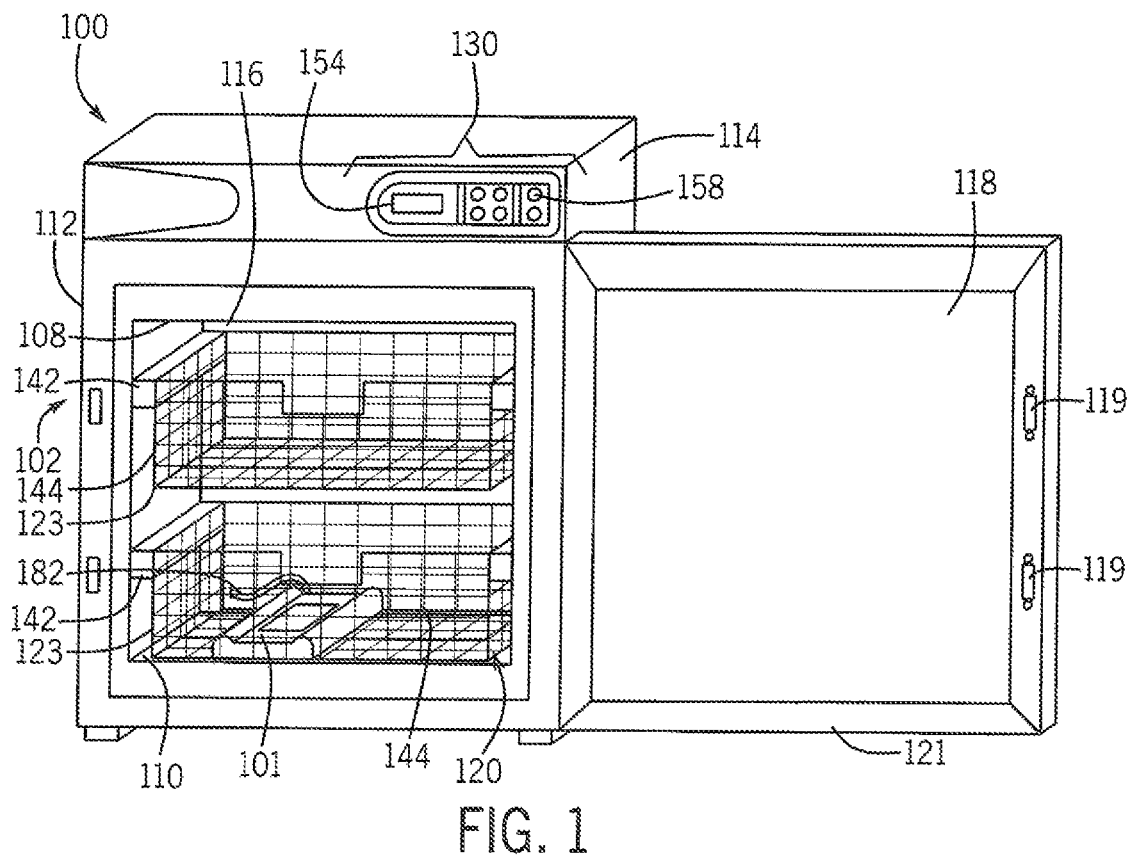
FIG. 1 is a cabinet projection of a warming cabinet of the present invention and used with an auxiliary temperature sensor connected at the inside of the cabinet and supported within a basket.

Referring to FIG. 1, a warming system 100 may include a warming cabinet 102 to be used to warm a variety of items, such as intravenous fluids, blankets, and medicines and nutriments. The warming cabinet 102 may be generally rectangular and include a plurality of walls including a top wall 108 in parallel opposition to a bottom wall 110. Left, right, and rear edges of the top wall 108 and bottom wall 110 are joined by a left wall 112, a right wall 114 and a rear wall 116 which together define an interior warming chamber volume 120. A door 118 is hingedly attached to the right wall 114 to be moved to a closed position sealing the interior warming chamber 120. The door 118 also may be opened to access the interior warming chamber 120. Latches 119 may be provided keep the door 118 closed and/or the door may include a spring biasing it toward a closed position. The door may also include a seal 121 (which may be a compressible gasket or the like) between the door 118 and the walls when the door 118 is closed.

One or more shelves 123 may be arranged in the interior heating chamber 120 providing horizontally extending and vertically spaced support services subdividing the volume 120 to provide support for the items to be warmed therein or to increase the holding capacity of the cabinet 102. The shelves 123 may be in the form of wire baskets 144 held on support ledges 142 extending inwardly from the interior of the walls of the cabinet 102. The baskets 144 may be made of interwoven wires 194 or metal rods with longitudinal rods connected by transverse wires which are spaced at intervals from one another. The baskets 144 may be supported by the support ledges 142 at varying vertical distances so that two or more baskets 144 may be vertically spaced or stacked within the cabinet 102. The baskets 144 can slide in and out of the interior heating chamber 120 to facilitate insertion and removal of the items within the baskets 144. The baskets 144 may carry the items to be warmed, such as intravenous fluid bags 106.

Figure 3:
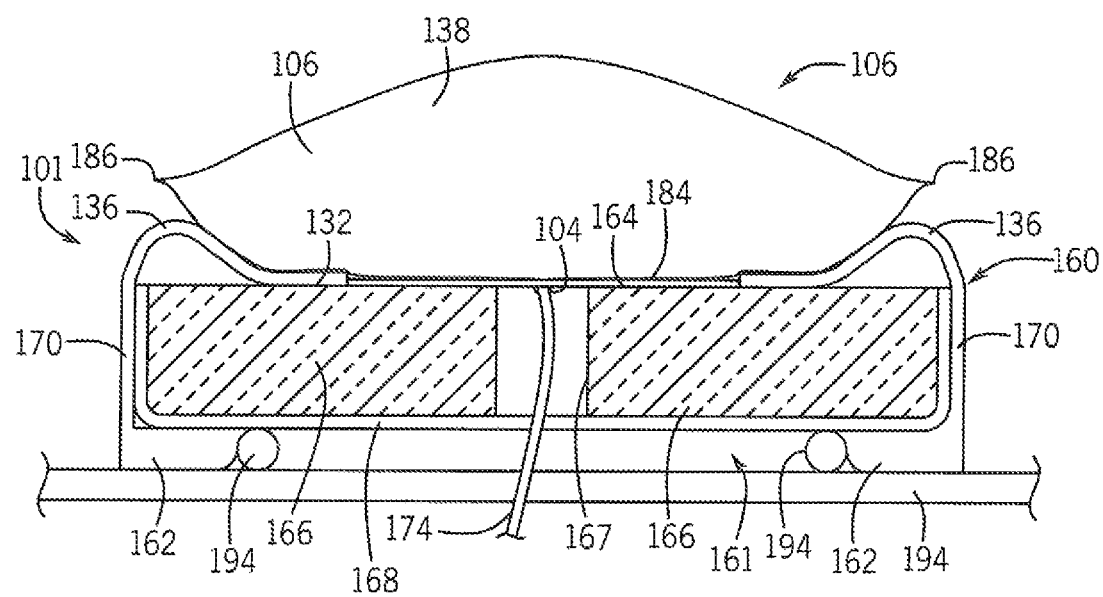
FIG. 3 is a cross section along line 3-3 of FIG. 2 showing an outer housing supporting a bag of intravenous fluid thereon, a heat collecting plate contacting the bag, a temperature sensor mounted to the underside of the heat collecting plate, and an insulating layer surrounding the temperature sensor, and where the outer housing is stabilized on lateral rods of the warming cabinet basket.

As is understood in the art, the intravenous fluid bags 106, shown in FIG. 3, may be constructed of a flexible transparent plastic material, such as a vinyl, and fabricated by joining two sheets 184 of the material at a peripheral seam 186 to provide within the seam 186 an enclosed pocket into which sterile infusion liquid 138 may be held.

Figure 4:
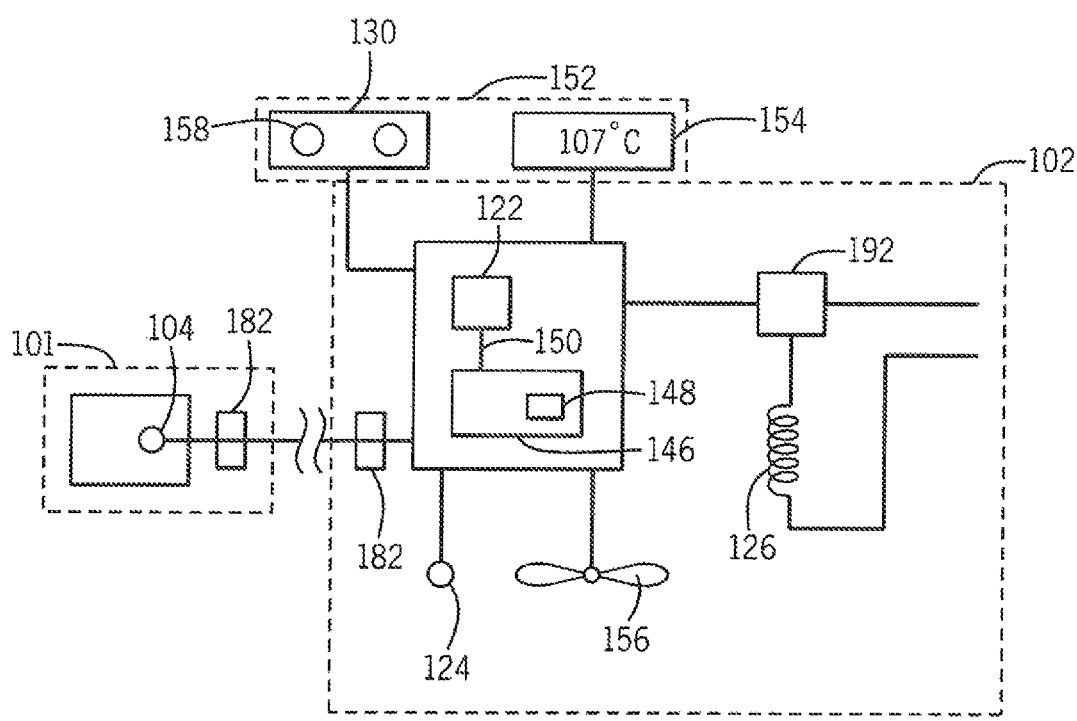
FIG. 4 is a block diagram of the functional components of the warming cabinet and the auxiliary temperature sensor in which the control provides a cabinet temperature or an auxiliary temperature.

Referring to FIG. 4, the warming system 100 further includes a computer 190 with a processor 122 communicating with a memory 146, the latter holding a program 148 providing an operating system for the warming cabinet 102 and specific executable programs for temperature display and calibration as will be described below. The processor 122 may communicate via various I/O lines 150 which also allow the processor 122 to control or monitor different components of the warming cabinet 102 including a user interface 152 with controls 130 and a visual display 154, circulating fan 156, controller 192 for heating elements 126, temperature sensor(s) 124, and auxiliary temperature sensor 104.

The processor 122 may communicate with the temperature sensor(s) 124, controller 192 for heating elements 126, and circulating fan 156 to regulate a temperature of the interior warming chamber 120 as understood in the art. The temperature sensors 124 may be mounted to the walls of the warming cabinet 102 by a bracket or adhesive. The processor 122 may detect an interior temperature of the interior warming chamber 120 via the temperature sensors 124 and turn the heating elements 126 on or off according to a desired warming chamber 120 temperature.

In one embodiment, the number of temperature sensors 124 may correspond with the number of heating zones within the interior warming chamber 120. For example, the processor 122 may be configured to independently monitor the temperature from temperature sensors 124 of each heating zone, and then further configured to independently control the heating elements 126 corresponding with each respective heating zone. This may be particularly useful when there is uneven warming within the interior warming chamber 120, for example, because of uneven loading of items within the cabinet. The heating elements 126 may be arranged as heating pad subassemblies as described in U.S. Pat. No. 8,581,152, assigned to the present applicant, and hereby incorporated by reference.

The processor may communicate with a circulating fan 156 that may assist to circulate the air within the interior warming chamber 120 and to assist with intake and exhaust of air into and out of the interior warming chamber 120. The circulation may help to reduce hot or cold spots within the chamber 120.

The processor 122 may communicate with a user interface 152 including a visual display 128 and one or more controls 130. The visual display 128 may be used in conjunction with the controls 130 to set the temperature of the interior warming chamber 120 and to show a set point temperature of the interior warming chamber 120 or of the individual heating elements 126. The controls 130 may also include a read out button 158 to switch the display from the set point temperature of the interior warming chamber 120 to current temperature conditions (i.e., the temperature of one or more of the heated zones) of the cabinet 102 or a temperature of the auxiliary temperature sensor 104.

Figure 2:
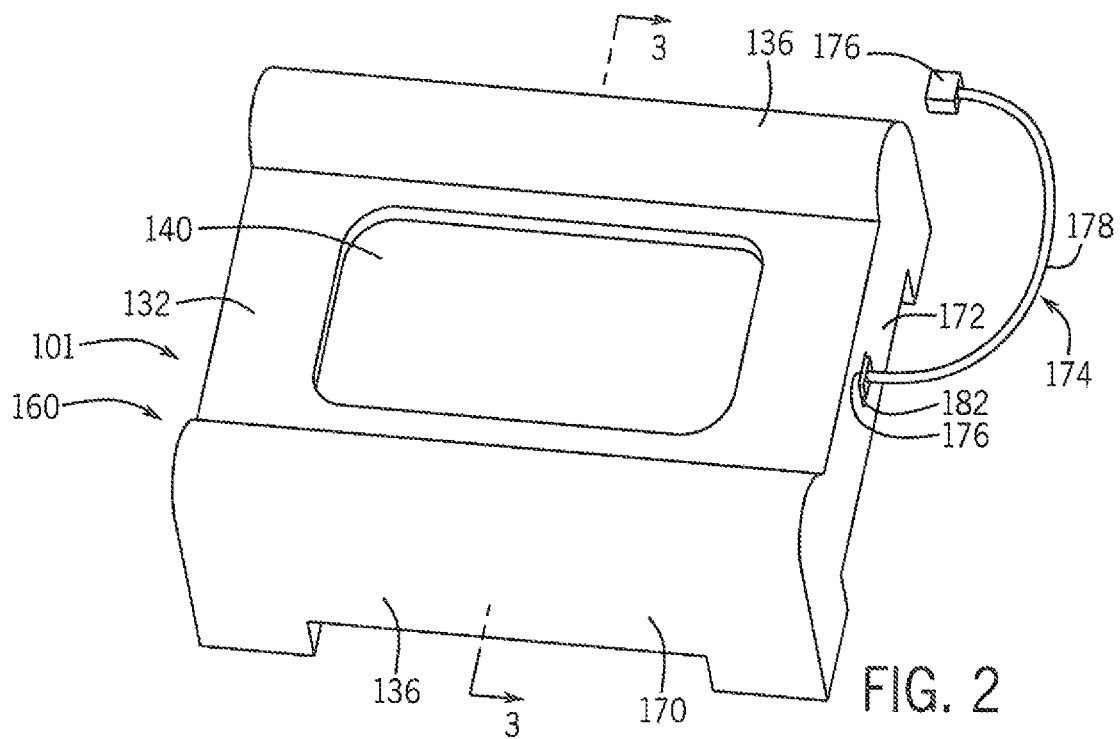
FIG. 2 is a perspective view, viewed generally from above, of the auxiliary temperature sensor of FIG. 1 with the connector disconnected from the cabinet.

Referring to FIGS. 1-3, the auxiliary temperature device 101 provides a generally rectangular housing 160. The housing 160 may have vertically extending sidewalls (such as two longer sidewalk 170 connected by two shorter sidewalls 172) and enclosed on a top end by a horizontal platform 132 for receipt of the intravenous fluid bag 106 thereon and a rectangular opening 140 to contact a heat collecting plate 164 within the opening 140 of the platform 132.

The platform 132 may be a generally rectangular horizontal ceiling, of the housing 160 and may be surrounded by curved concave rails 136 extending upwardly from the platform 132 along the outer edges of the longer sidewalk of the platform 132. For example, the curved rails 136 may be semi-cylinders. The curved rails 136 generally cradle an intravenous fluid bag 106 situated on the platform 132.

The platform 132 also provides a rectangular opening 140 centered within the ceiling to expose the heat collecting plate 164 below the opening 140. The opening 140 allows the intravenous fluid bag 106 to contact the heat collecting plate 164 disposed within an interior of the housing 160 as further explained below.

In one embodiment, the platform 132 may be approximately 3 inches long by 4 inches wide or less than than 15 square inches or less than than 12 square inches. The platform 132 may be sized to contact less than 75 percent of the lower surface area of the intravenous fluid bag 106. In this, respect, the edges of the intravenous fluid bag 106 may extend past the edges of the housing 160 while a center of the bag is substantially supported by the housing 160.

In one embodiment, the opening 140 may be approximately 3 inches long by 2 inches wide or greater than 4 square inches or greater than 6 square inches. The opening 140 or exposed area of the heat collecting plate 164 may be sized to contact at least 30% of the lower surface area of the intravenous fluid bag 106. In this respect, the contact area is large enough to facilitate, conduction from the intravenous fluid bag 106 to the heat collecting plate 164.

Referring to FIG. 3, disposed within the housing 160, and centered within the opening 140 of the platform 132 and generally pressed up against the upper opening 140, is a heat collecting plate 164 contacting the intravenous fluid bag 106 when the intravenous fluid bag 106 is placed on the platform 132. The heat collecting plate 164 may be a thin sheet of conductive metal, such as aluminum or copper, which contacts the intravenous fluid bag 106 and conducts the heat from the intravenous fluid bag 106. The plate may have a minimal gauge thickness (e.g., about 0.01 inches or less than 0.1 inches) to provide low thermal mass (e.g., heat capacity of 003-0.09 J/gm K) to accelerate temperature measurement and has high conductivity.

An auxiliary temperature sensor 104 may be mounted to the underside of the heat collecting plate 164 and be positioned approximately in the center of the opening 140 to be near a center region of the contact with the intravenous fluid bag 106. The auxiliary temperature sensor 104 may be mounted to the heat collecting plate 164 using an epoxy resin to provide good heat conductivity between the heat collecting plate 164 and the temperature sensor 104.

The temperature sensor 104 detects an approximately average temperature, of the heat collecting plate 164. It is contemplated that more than one temperature sensor may be used and their temperature readings averaged to approximate a heat collecting plate temperature. Temperature sensor 104 may be, for example, a thermocouple, a thermistor, a resistive temperature device, or other similar temperature sensing devices. As will be noted below, high linearity is not required because of the calibration system and the ability to process the received temperature signal with the processor 122.

It is understood that the flexible material of the intravenous fluid bag 106 permits the intravenous fluid bag 106 to adopt a variety of different volumetric configurations, and the shape of the platform 132 is designed to promote contact of the intravenous fluid bag 106 with the temperature sensor 104.

An undersurface of the heat collecting plate 164 and the auxiliary temperature sensor 104 is supported by and surrounded by an insulating material 166 reducing the temperature drop between the intravenous fluid bag 106 and the auxiliary temperature sensor 104. The insulating material 166 may be a Styrofoam or other insulating foam material.

The insulating material 166 may be supported and sandwiched by a lower panel 168 thereby supporting the heat collecting plate 164, auxiliary temperature sensor 104, and insulating material 166 against the force of the intravenous fluid bag 106 thereon. The lower panel 168 may be constructed of a metal sheet defining a floor of the housing 160 held in by the vertical sidewalls 170, 172 of the molded plastic housing 160. The lower panel 168 may be a substantially U-shaped frame or four sided box frame containing upwardly extending sidewalls surrounding a floor with the insulating material 166 carried within or between the sidewalls.

A channel 167 may extend through the insulating material 166 allowing an electrical connector 174 to extend from the temperature sensor 104 to an exterior of the housing 160, for example, through a releasable electrical connector or jack 182.

The vertical sidewalls 170, 172 supporting the horizontal platform 132 of the housing 160 may be shaped so as to provide downwardly extending feet 162 at the lower corners of the housing 160 to lift and support the housing 160 on a table, shelf, basket, or the like. The feet 162 may curved around the lower corners of the housing 160 with carve-outs 161 extending along the lengths of the housings between the feet 162.

In one embodiment, when the auxiliary temperature device 101 is supported in the basket 144, as shown in FIGS. 1 and 3, the carve-outs 161 provided between adjacent feet 162 allows the auxiliary temperature device 101 to rest on the spaced wire 194 or metal rods of the baskets 144 without unwanted movement. In particular, the interval between longitudinal rods of the basket or length of the carve-outs 161 may correspond with the space between adjacent feet 162 of the housing 160.

Generally the housing 160 and platform 132 will be fabricated from injection molded thermoplastic or the like.

Referring to FIGS. 1 and 2, in operation, the auxiliary temperature device 101 may be connected to the warming cabinet 102 through a releasable electrical connector or jack 182 on the interior or exterior wall of the warming cabinet 102 to communicate with the processor 122 of the warming cabinet 102. The connection may be made via an electrical connector 174 having first and second modular connectors 176, similar to telephone plugs, at opposite ends of the connector cord 178. The modular connectors 176 are insertable into, a mating socket or jack 182. The first modular connector 176 is insertable into a jack 182 of the cabinet 102 and the second modular connector 176 is insertable into a jack 182 of the auxiliary temperature device 101, connecting the auxiliary temperature device 101 to the warming cabinet 102. The connector cord 178 may be coiled, similar to a coiled telephone cord, allowing it to be flexible and extensible from the warming cabinet 102.

The jack 182 of the cabinet 102 may be located on an interior wall of the interior warming chamber 120, such as a lower end of the rear wall 116, or on an exterior wall of the warming cabinet 102, or in both positions to allow the auxiliary temperature device 101 to be used in both configurations. The jack 182 of the auxiliary temperature device 101 may be on a sidewall 172. When the auxiliary temperature device 101 is connected inside the interior heating chamber 120, the device may be positioned within the chamber 120 such as on shelf 123, within the basket 144, or on the floor 110 of the chamber 120. When the auxiliary temperature device 101 is connected to an exterior wall, the device 101 may be positioned on top of the warming cabinet 102, a table besides the warming cabinet 102, or elsewhere near to the warming cabinet 102 during use.

It is contemplated that the temperature sensor 104/auxiliary temperature device 101 and processor 122 may also communicate through a wireless communication standard, such as Bluetooth, Wi-Fi, and the like, as understood in the art.

When the user desires a temperature of the intravenous fluid, bag 106 to be measured, the intravenous fluid bag 106 is placed on the platform 132, as seen in FIG. 3. In particular, the platform 132 is shaped to support the intravenous fluid bag 106 with one lower sheet 184 of the intravenous fluid bag 106 lying in close abutment to the platform 132. In this way, contact between the intravenous fluid bag 106 and the heat collecting plate 164 may be, substantially maximized and the thermal path between the fluid and the sensor substantially maximized. The edges of the intravenous fluid bag 106 may be cradled by the rails 136 so that a width of the bag lies substantially within the platform 132 while a length of the bag may extend outwardly past an edge of the platform 132.

Figure 5:
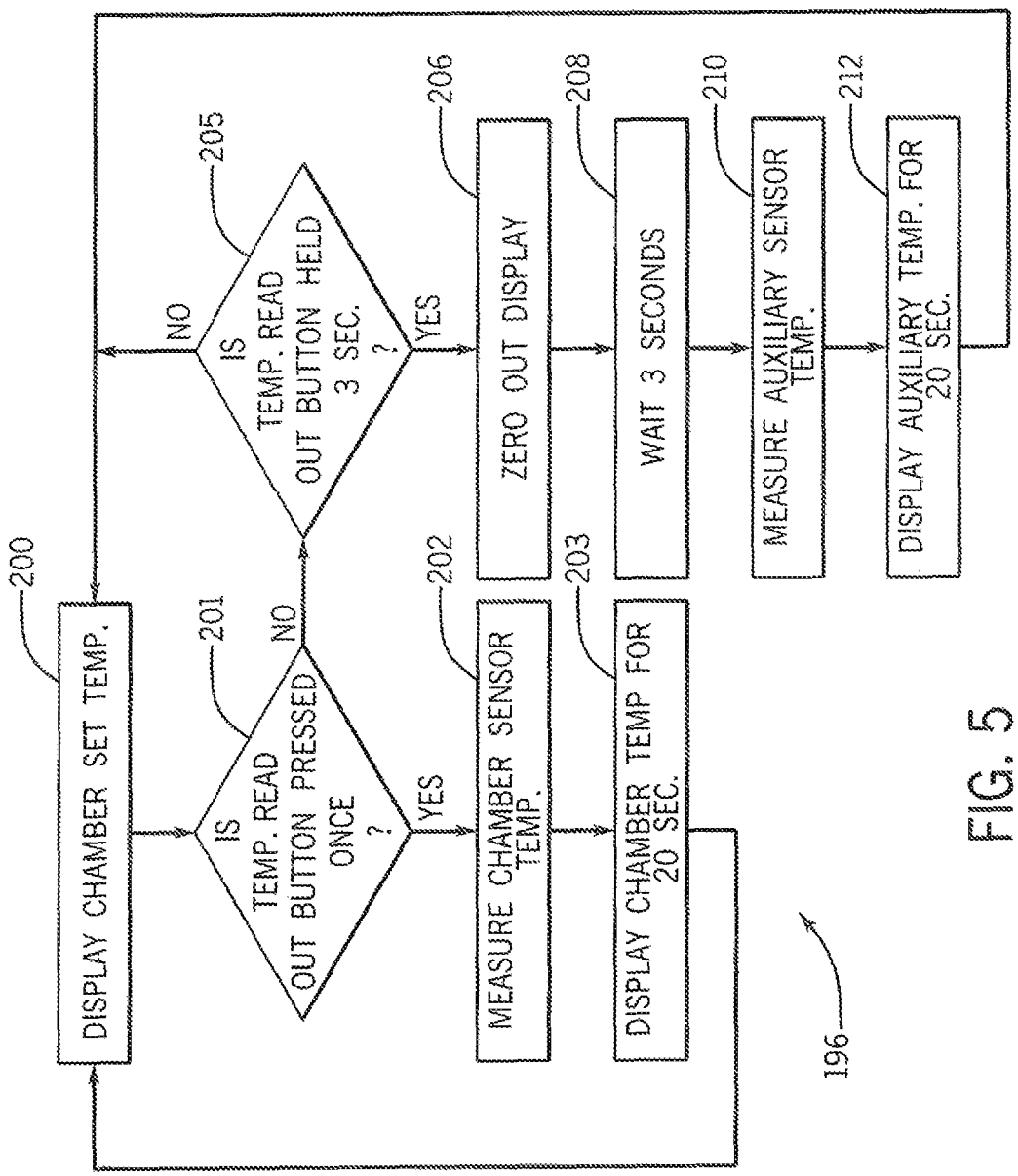
FIG. 5 is a flow chart of the steps of operation of the warming cabinet of FIGS. 1-4 in implementing the present invention to selectively display the cabinet temperature of the cabinet sensor or auxiliary temperature of the auxiliary temperature sensor.

Referring to FIG. 5, the processor 122 operates to display a temperature of the interior heating chamber 120 or an, auxiliary temperature device 101, as provided in the sequence of process steps shown as 196, when activated by the user.

As indicated by process block 200, the processor 122 normally displays a chamber set point temperature (i.e., the temperature at which the user sets or programs the cabinet).

As shown in process block 201, the processor 122 may determine whether a read out button 158 is pressed. If the read out button 158 has been pressed once, the processor 122 will receive a temperature signal measured from the chamber temperature sensor 124 indicating a temperature of the interior heating chamber 120 as shown in process block 202.

The processor 122 will then display a current state temperature (i.e., the temperature of one or more of the heated zones) of the cabinet 102 via the temperature sensors 124 of the interior heating chamber 120 and display it on the visual display 128 for a predetermined time period, as shown in process block 203. For example, the predetermined time may be 20 seconds or 10-20 seconds. Alternatively, the current state temperature may continue to be shown until the user presses a control button 130, such as read out button 158 once again, to switch the temperature signal input from the temperature sensors 124 back to the chamber set point temperature.

If the read out button has not been pressed once, the processor 122 may proceed to process block 205. As shown in process, block 205, the processor 122 may determine whether read out button 158 has been pressed for a predetermined time period, e.g., for more than three seconds. If so, the processor 122 will proceed to step 206.

As indicated by process block 206, when the user indicates that he or she would like to determine an auxiliary device temperature by pressing the read out button 158 for a predetermined time period, e.g., three or more seconds, the visual display 128 will be zeroed out and will no longer display the chamber set temperature.

As indicated by process block 208, the processor 122 will wait a predetermined time period, such as three or three to five seconds, to allow time for heat transfer from the intravenous fluid bag 106 to the heat collecting plate 164 and to accommodate the response time of the auxiliary temperature sensor 104. As is understood in the art, the program may extrapolate an asymptotic temperature value from a short measurement time.

As indicated by process block 210, after the predetermined time has passed, the processor 122 receives a temperature signal measured from the auxiliary temperature sensor 104 indicating a temperature of the intravenous fluid bag 106.

As indicated by process block 212, the temperature of the intravenous fluid bag is displayed on the visual display 128. The auxiliary temperature sensor 1 temperature may be displayed for a predetermined time period, for example, 20 seconds or 10-20 seconds, before returning to process block 200. Alternatively, auxiliary temperature may continue to be displayed until the user presses a control button 130, such as read out button 158, to switch the temperature signal input from the auxiliary temperature sensor 104 back to chamber set point temperature.

Figure 6:
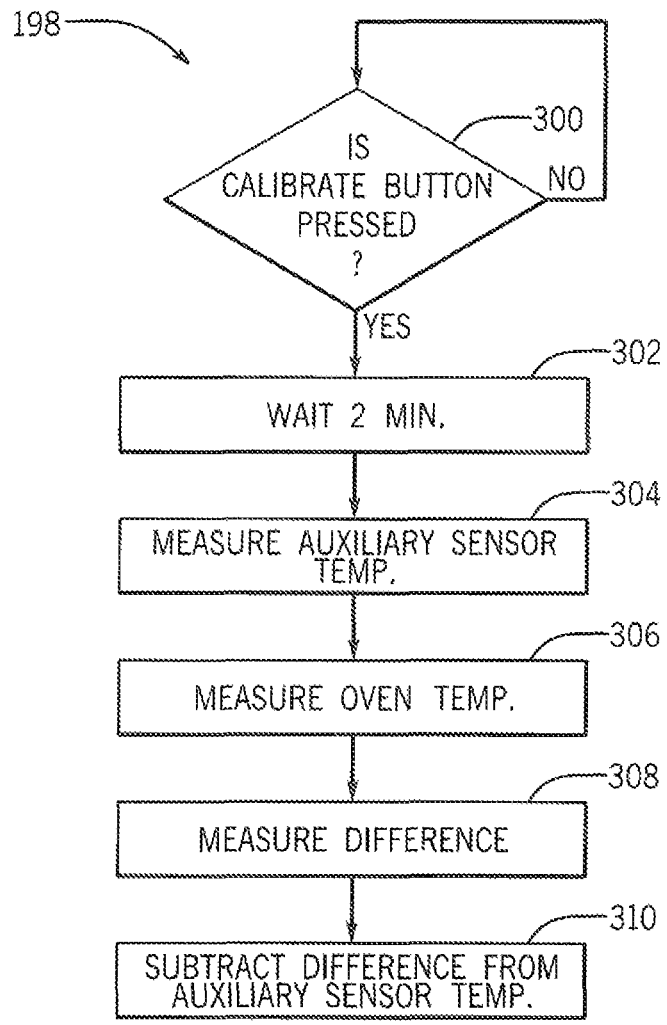
FIG. 6 is a flow chart of the steps of operation of the warming cabinet of FIGS. 1-4 in implementing the present invention to calibrate the auxiliary temperature sensor.

Referring to FIG. 6, optionally as shown in 198, the auxiliary temperature sensor 104 may be calibrated before use by placing the auxiliary temperature device 101 within an empty warming cabinet 102. When the auxiliary temperature device 101 is connected to the warming cabinet 102, the processor 122 will determine whether the user has initiated calibration by pressing the calibrate button of the user interface 152, as seen in process block 300. If calibration is initiated by the user, then the process will continue to process block 302. If calibration is not initiated, then process block 300 is repeated until the calibrate button is pressed.

As indicated by process block 302, once calibration is initiated, the process waits a designated amount of time, such as two or one to five minutes, to allow the auxiliary temperature device 101 to reach the interior heating chamber 120 temperature. Again an asymptotic temperature value may be extrapolated.

As indicated by process block 304, after the auxiliary temperature device 101 has reached the same temperature as the chamber 120, then a temperature measurement is taken at the auxiliary temperature sensor 104.

As indicated by process block 306, the processor proceeds to take a temperature measurement of the interior heating chamber 120 at the temperature sensors 124 at the walls of the interior heating chamber 120. As indicated by process block 308, the temperature measurement at the auxiliary temperature sensor 104 and at the temperature sensors 124 are compared and a difference is measured.

As indicated by process block 310, this difference is subtracted from the reading at the auxiliary temperature sensor 104 to "zero the offset" of the auxiliary temperature sensor 104 and calibrate the temperature for any future temperature readings.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a controller" and "a processor" should be understood to include one or more microprocessors that can communicate in, a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

What we claim is:

1. An auxiliary temperature monitoring system for measuring the temperature of an IV bag held within a warming cabinet, the system comprising:
    a housing having an internal cavity;
    at least one electric heater fixed to the housing and adapted to heat the internal cavity;
    a sensor detecting a temperature of air of internal cavity and communicating with the at least one electric heater to control a temperature of the internal cavity; and
    an auxiliary temperature device repositionable within the internal cavity independent of a position of all electric heaters, the auxiliary temperature device-comprising:
        an auxiliary housing,
        a heat collection plate supported by the housing and having an upwardly exposed upper surface configured to support an IV bag thereon opposite a lower surface supporting an insulating layer, the insulating layer positioned between the heat collection plate and the air of the cavity and configured to block heat transfer from the air of the cavity to the lower surface of the heat collection plate, and
        an auxiliary sensor supported by the heat collection plate and configured to provide a temperature of the IV bag substantially independent of the temperature of the air of the internal cavity.

2. The system of claim 1 further comprising a feedback control system receiving the temperature of the internal cavity from the sensor to control activation of the heater.

3. The system of claim 1 wherein the plate is sized to contact at least 30 percent of a lower surface of an IV bag supported by the auxiliary housing.

4. The system of claim 3 wherein the heat collection plate has an exposed area greater than 4 square inches.

5. The system of claim 4 wherein the exposed area of the heat collection plate is greater than 6 square inches.

6. The system of claim 1 wherein an entire lower surface of the auxiliary housing beneath the heat collection plate is insulated.

7. The system of claim 1 wherein the upper surface of the housing has opposed rails along opposite sides of the housing upper surface configured to retain the IV bag.

8. The system of claim 1 wherein an interior surface of the internal cavity has a releasable electrical connector adapted to receive a first end of a mating second electrical connector connected to the auxiliary temperature device.

9. The system of claim 8 wherein the second electrical connector communicates with the auxiliary temperature device through a flexible conductor.

10. The system of claim 8 wherein an exterior surface of the housing has a third electrical connector adapted to receive the second electrical connector wherein an opposite end is connected to the auxiliary temperature device.

11. The system of claim 1 further comprising a processor operating a program stored in memory to communicate with the auxiliary sensor to determine an average temperature of the heat collection plate.

12. The system of claim 11 wherein the processor operates the program stored in memory to communicate with a read out button to display the temperature of the auxiliary sensor on a cabinet display screen.

13. The system of claim 12 wherein the processor further operates the program stored in memory to communicate with a calibration button to compare the temperature of the sensor with the temperature of the auxiliary sensor and subtract a difference between the temperature of the sensor and the temperature of the auxiliary sensor from the temperature of the auxiliary sensor to calibrate the auxiliary sensor.

14. The system of claim 1 wherein the housing is supported on feet extending downwardly from a bottom of the housing that are spaced to engage wire racks of the internal cavity therebetween the feet.

15. The system of claim 1 wherein the auxiliary temperature device does not have a heater.

16. The system of claim 1 wherein the housing is sized to contact less than 75 percent of a lower surface of the IV bag supported by the auxiliary housing.

17. The system of claim 1 wherein the sensor is bonded beneath the heat collection plate.

18. The system of claim 1 wherein the heat collection plate is a conductive metal.

19. The system of claim 1 wherein the heat collection plate has a gauge thickness of less than or equal to 0.01 inches.

20. A method of detecting a temperature of an IV bag placed within a warming cabinet comprising a housing having an internal cavity; at least one electric heater fixed to the housing and adapted to heat the internal cavity; and a sensor detecting a temperature of air within the internal cavity and communicating with the at least one electric heater to control a temperature of the internal cavity, wherein the temperature is independent of a temperature of the warming cabinet, comprising the steps of:

placing an auxiliary temperature device comprising an auxiliary housing, a heat collection plate supported by the housing and having an upwardly exposed upper surface configured to support an IV bag thereon opposite a lower surface supporting an insulating layer, the insulating layer positioned between the heat collection plate and the air of the cavity and configured to block heat transfer from the air of the cavity to the lower surface of the heat collection plate, and an auxiliary sensor supported by the heat collection plate and configured to provide a temperature of the IV bag substantially independent of the temperature of the air of the internal cavity within the warming cabinet wherein the auxiliary temperature device is repositionable within the internal cavity independent of a position of all electric heaters within the internal cavity;

connecting the auxiliary temperature device to the warming cabinet;

placing the IV bag on the heat collection plate;

pressing a temperature read out button; and displaying the temperature of the heat collection plate on a display.

\* \* \* \* \*